United States Patent [19]

Brewer

[11] Patent Number: 4,924,881
[45] Date of Patent: May 15, 1990

[54] IMPLANTABLE ENDOCARDIAL LEAD WITH FIXATION DEVICE RETRACTABLE BY THREADED STYLET

[75] Inventor: Maurice A. Brewer, Houston, Tex.
[73] Assignee: Intermedics, Inc., Angleton, Tex.
[21] Appl. No.: 351,444
[22] Filed: May 12, 1989
[51] Int. Cl.⁵ .............................................. A61N 1/05
[52] U.S. Cl. ..................................... 128/785; 128/786
[58] Field of Search ................................ 128/784–786, 128/419 P

[56] References Cited

U.S. PATENT DOCUMENTS

| | | | |
|---|---|---|---|
| 3,754,555 | 8/1973 | Schmitt | 128/785 |
| 4,280,512 | 7/1981 | Karr et al. | 128/785 |
| 4,475,560 | 10/1984 | Tarjan et al. | 128/785 |
| 4,624,266 | 11/1986 | Kane | 128/785 |
| 4,649,938 | 3/1987 | McArthur | 128/785 |

FOREIGN PATENT DOCUMENTS

| | | | |
|---|---|---|---|
| 2736275 | 2/1979 | Fed. Rep. of Germany | 128/785 |
| 2806069 | 8/1979 | Fed. Rep. of Germany | 128/785 |

*Primary Examiner*—Lee S. Cohen
*Attorney, Agent, or Firm*—John R. Merkling

[57] ABSTRACT

An implantable endocardial lead with retractable fixation device. The fixation device comprises a sharpened helix which can be repeatedly both retracted within a distal end of the lead and displaced outside the lead. A threaded stylet passes through a lumen from a proximal end of the lead to the distal end of the lead, where the threaded stylet is screwed into a piston supporting the helix. When the helix is in an exposed position, torque can be transmitted from the proximal end of the lead through the distal end to the piston and thence to the helix to screw the helix into the endocardial tissue.

5 Claims, 4 Drawing Sheets

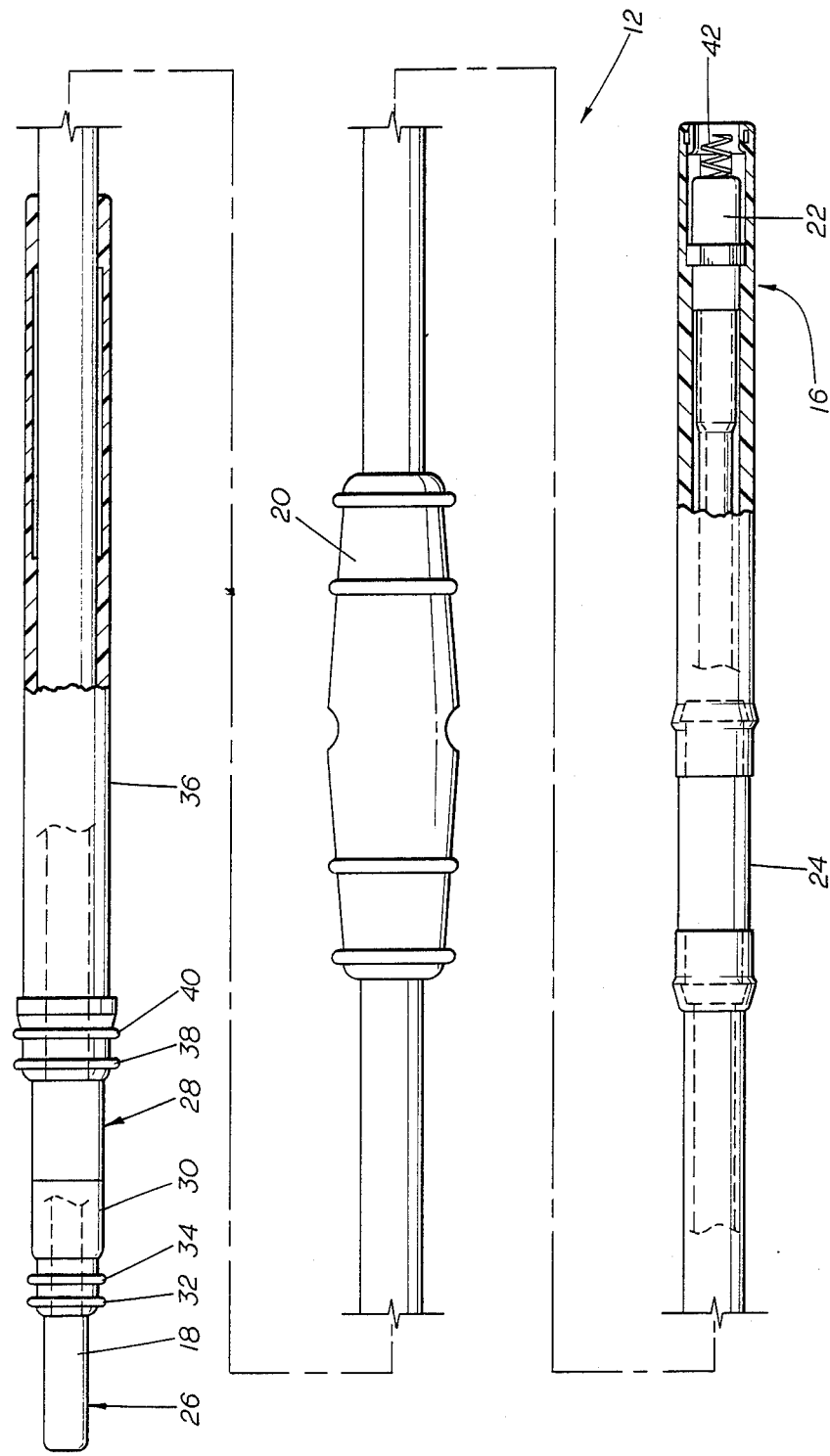

IMPLANTABLE ENDOCARDIAL LEAD WITH FIXATION DEVICE RETRACTABLE BY THREADED STYLET

BACKGROUND OF THE INVENTION

1. Field of the Invention

The present invention relates generally to cardiac stimulation, and more particularly to an implantable endocardial lead which stimulates or senses electrical activity of the heart and which employs a retractable fixation mechanism which can be repeatedly exposed to or shielded from tissue during the process of securing the lead to cardiac tissue.

2. Prior Art

There are generally two types of body implantable leads used with cardiac pacemakers —one which requires surgery to expose the myocardial tissue to which an electrode is affixed and another which can be inserted through a body vessel, such as a vein, into the heart where an electrode contacts the endocardial tissue. In the latter type, the endocardial lead is often secured to the heart through the endothelial lining by a sharpened helix affixed to a distal end of the lead. When the end of the lead contacts the lining of the heart at a desired location, the lead may be secured in place by rotating the lead, thus screwing the helix into the heart tissue.

Such a system has been relatively effective in securing an endocardial lead once the initial location of the lead has been achieved. However, it is known that it can be undesirable to expose the sharpened helix while the lead is being inserted through a blood vessel into the heart. Moreover, it is difficult to precisely place an endocardial lead on the first attempt. It is common, therefore, for a physician to repeatedly attempt to attach an endocardial lead having a sharpened helix securing means. It is desireable, therefore, to be able to shield the sharpened helix during the insertion of the lead through the vein and between attempts to implant the lead on the heart lining.

In the prior art, various apparatus have been proposed for achieving the desired result. For example, U.S. Pat. No. 3,974,834 to Lawrence M. Kane, discloses an implantable intervascular lead having an accordion-fold sleeve surrounding a helix. The sleeve is retractable to expose the helix and re-expandable to cover the helix in the event the helix is unscrewed and withdrawn. An object of the invention is to permit the lead to be inserted into and guided through a body vessel without snagging the body vessel.

Another attempt at solving these problems is disclosed in U.S. Pat. No. 4,146,036 to Robert G. Dutcher and Albert S. Benjamin. This patent discloses a body implantable, intervascular lead, having a helix fixation means. Apparatus for shielding the helix comprises a moveable piston or shaft located within the coils of the helix. The shaft is spring-loaded in a retracted position by the action of an elastomeric boot which also serves to seal off body fluids from the interior of the lead. A stylet passes through a lumen in the lead and acts against a proximal end of the shaft to force the shaft forward through the helix thus forming a partial barrier and inhibiting the helix from coming in contact with tissue, at least in the axial direction.

In U.S. Pat. No. 4,649,938 to William A. McArthur, an endocardial lead with a extendible/retractable helix fixation means is described. The helix is mounted on a bobbin carried within the electrode tip. The bobbin and helix are retracted into the electrode tip by the action of a spring and are extended out of the tip by pressure from the end of the stylet inserted through a lumen in the lead.

SUMMARY OF THE INVENTION

The present invention provides an implantable endocardial lead with retractable fixation means. In the preferred embodiment, the fixation means comprises a sharpened helix which can be repeatedly both retracted within a distal end of the lead and displaced outside the lead. The lead defines a lumen from its proximal to its distal end. A threaded stylet passes through the lumen from the proximal end of the lead to the distal end of the lead, where the threaded stylet is screwed into a piston supporting the helix. By moving the stylet, the helix can be displaced outside or retracted within the lead, but the helix is not rotated by the stylet in relation to the lead. When the helix is in an exposed position, torque can be transmitted from the proximal end of the lead through the distal end to the piston and thence to the helix to screw the helix into the endocardial tissue.

It is a principal object of the present invention to provide an implantable endocardial lead with retractable fixation means wherein the fixation means can be repeatably shielded and exposed during the implantation process.

A further object of the invention is to provide a lead wherein the fixation means is selectively shielded within the distal end of the lead and wherein the fixation means is selectively exposed and shielded by the action of a threaded stylet.

These and other objects and features of the present invention will be apparent from the detailed description taken with reference to the accompanying drawings.

BRIEF DESCRIPTION OF THE DRAWINGS

FIG. 2 is a partial cross-section of selected portions of the lead of FIG. 1;

DETAILED DESCRIPTION OF THE PREFERRED EMBODIMENT

Figure 1:
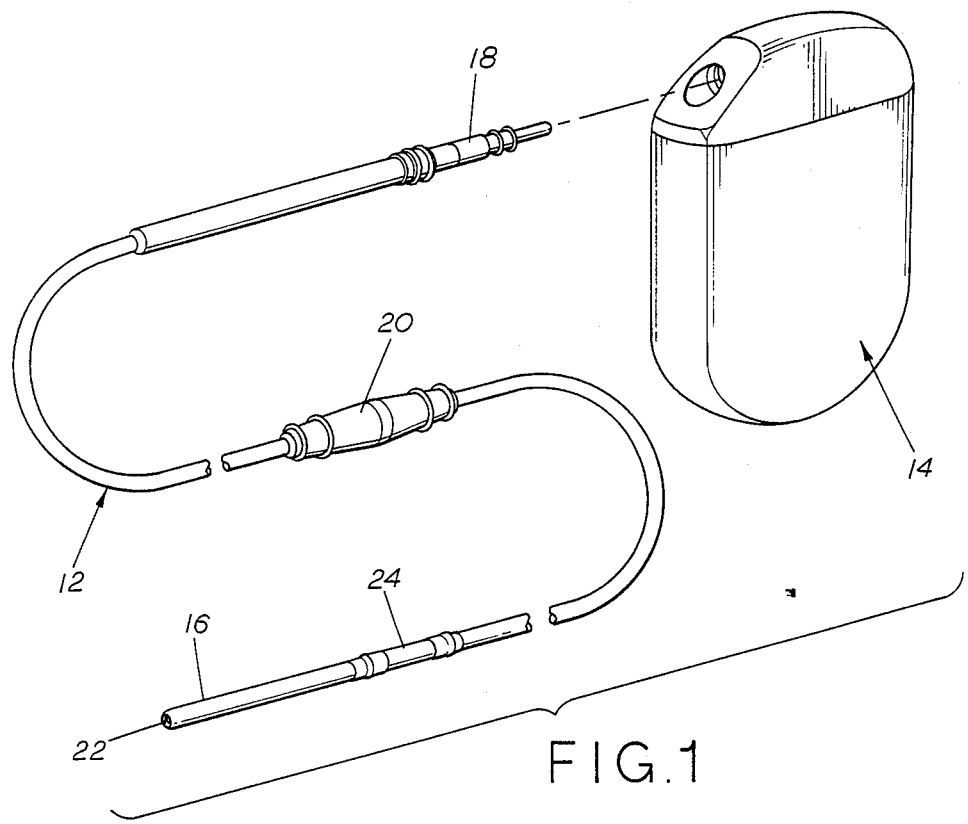
FIG. 1 is a prospective view of an implantable bipolar endocardial lead according to the present invention.
Figure 4:
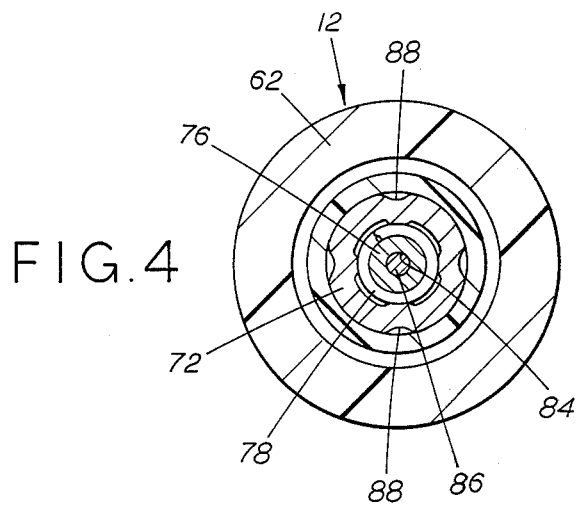
FIG. 4 is a cross-sectional view taken along line 4—4 of FIG. 3.

Reference is now made to the drawings, wherein like numerals designate like parts throughout. FIG. 1 shows an assembly, comprising an endocardial lead 12 and cardiac pacer 14. The endocardial lead 12 has a proximal end 18 and a distal end 16. The lead 12 has a suture sleeve 20 which slides along the lead 12 and which can be attached at an entrance into a vein of a patient in a conventional manner. The lead 12 also has both a tip electrode 22 located near the distal end 16 of the lead and a band electrode 24 spaced away from the tip electrode 22.

Referring now to FIG. 2, the proximal end 18 of the lead 12 comprises a plug 26 which provides a first electrical connection to the pacer 14. A contact plate 28 is also located near the proximal end 18 of the lead 12 and provides a second electrical contact for the pacer 14. Between the contact plate 28 and the plug 26 there is a silicone insulator 30 having two annular seals 32, 34. On the distal side of the contact plate 28, there is a silicon jacket 36, which also has two annular seals 38, 40. The annular seals 32, 34, 38 and 40 exclude body fluids from the pacer 14 when the lead 12 is inserted into the pacer 14.

Figure 3:
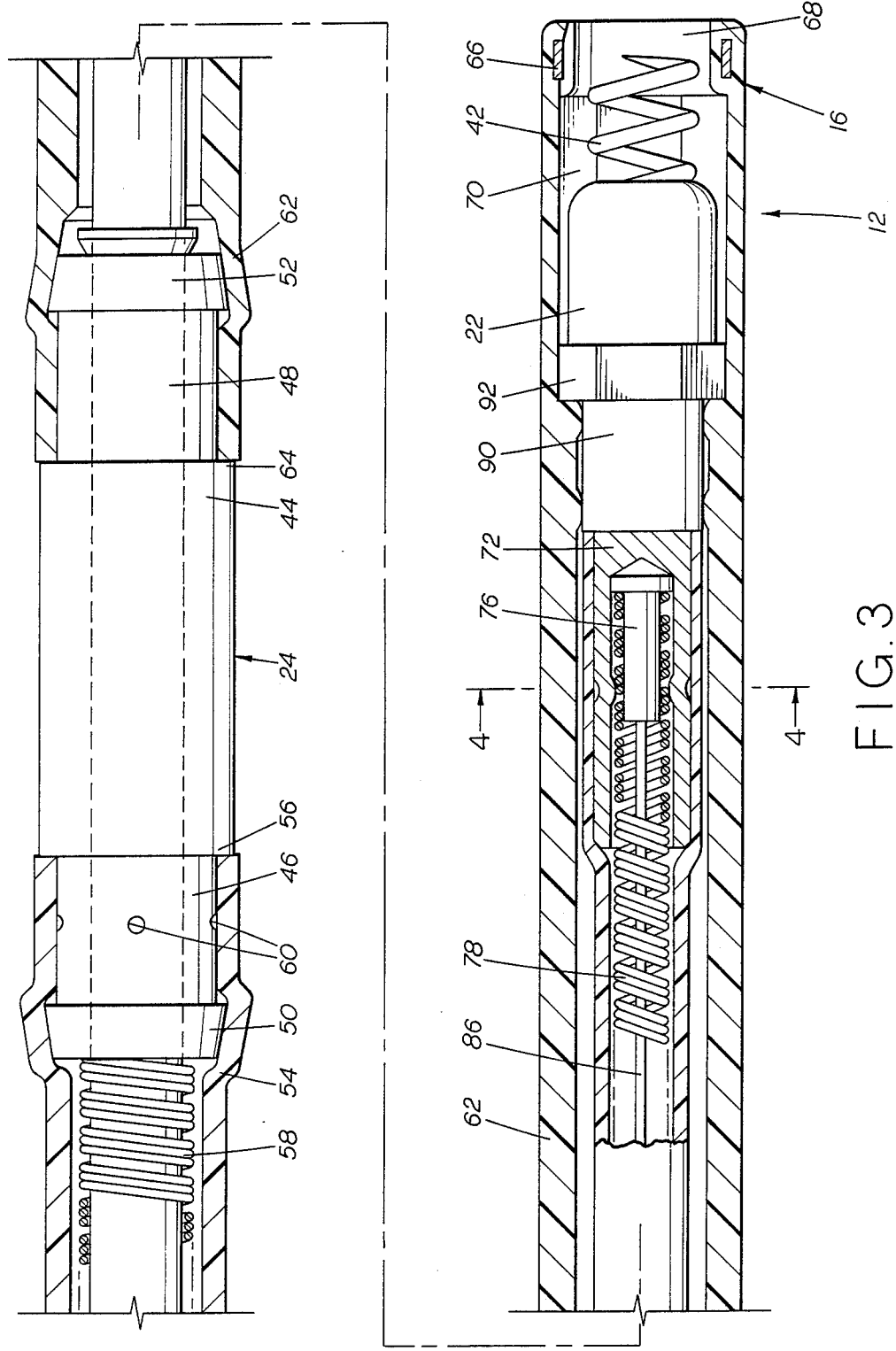
FIG. 3 is a cross-sectional view of a tip electrode and a band electrode of the lead.
Figure 5:
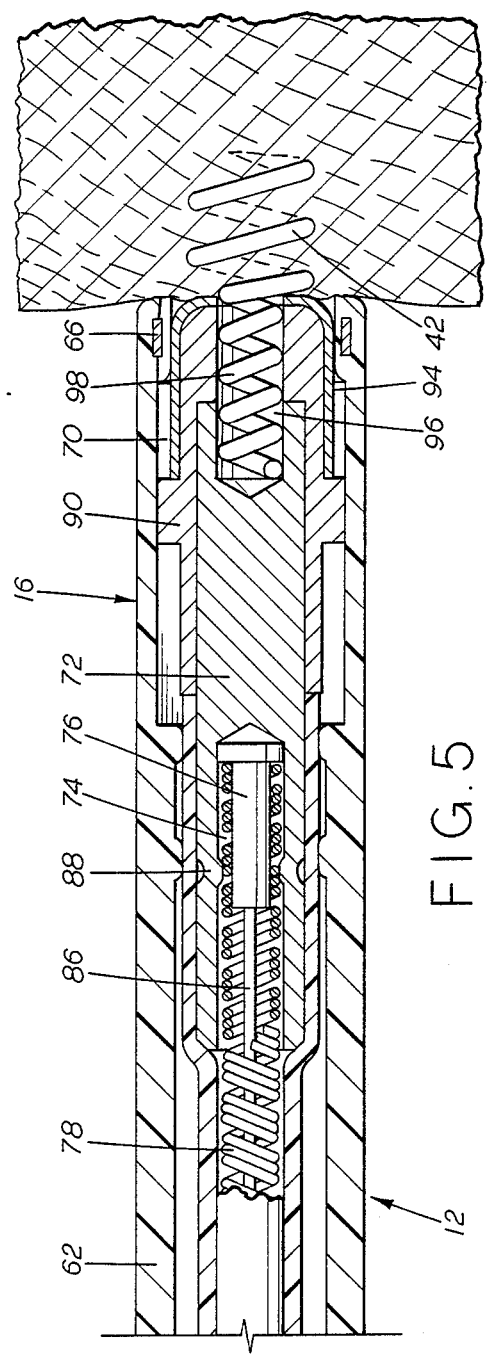
FIG. 5 is a cross-sectional view of the tip electrode implanted in heart tissue.
Figure 6:
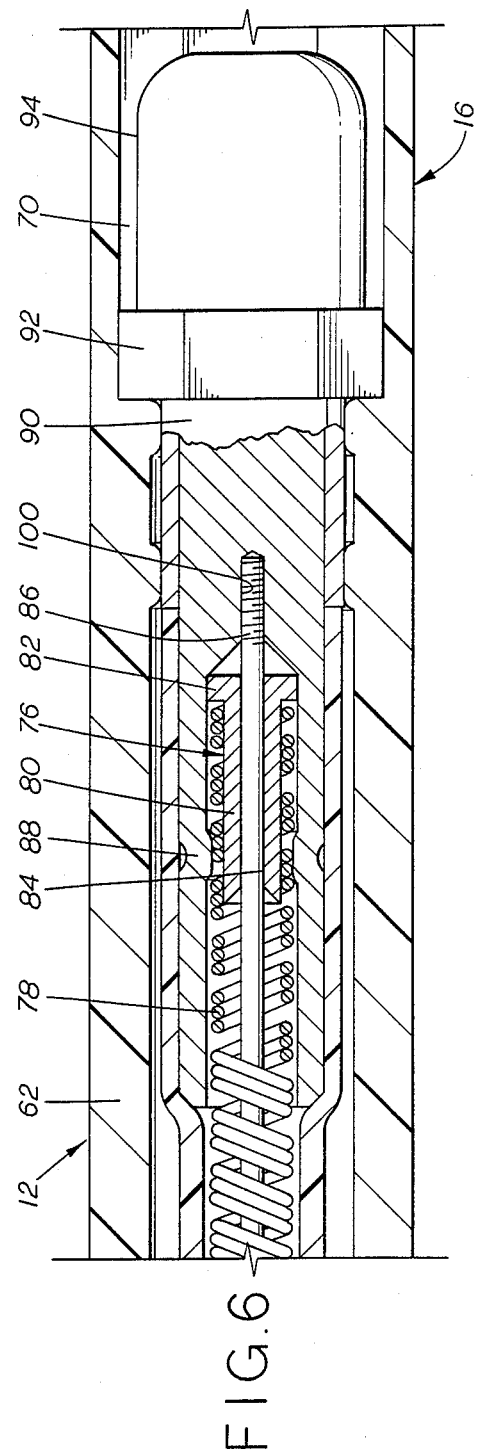
FIG. 6 is a cross-sectional view of the tip electrode showing the attached threaded stylet.

In a bi-polar endocardial lead, both the band electrode 24 and the tip electrode 22 are at the distal end 16. In the preferred embodiment, the tip electrode 22 comprises a sharpened helix 42 which can be screwed into a patient's myocardial tissue. FIG. 3 shows an enlarged cross-section of the band electrode 24 and the tip electrode 22. The band electrode 24 comprises a tubular conductor 44 having tubular tenons 46, 48 at each end. Each tenon 46, 48 has an annular lip 50, 52 spaced away from the tubular conductor 44. A silicone sleeve 54 extends from the contact plate 28 at the proximal end 18 of the lead 12 to a shoulder 56 between the proximal tenon 46 and the tubular conductor 44. Electrical impulses are carried from the contact plate 28 to the band conductor 24 by a filar coiled conductor 58. Electrical contact is maintained between the band electrode 24 and the trifilar conductor 58 by spot crimps 60.

At the distal end of the band electrode 24, a silicone sheath 62 extends from a shoulder 64 between the tubular conductor 44 and the distal tenon 48 to the distal end 16 of the lead 12. At the distal end 16, the silicone sheath is stiffened by an implantable ring 66. A constricted opening 68 is formed in the end of the lead 12. On the, proximal side of the constricted opening 68 there is a hexagonal chamber 70.

The tip electrode 22 slides but does not rotate inside the silicon sheath 62. The tip electrode 22 comprises a conductive element 72 having a bore 74 in the proximal end thereof for receiving a crimp slug 76 and a tight-wound trifilar coiled conductor 78. The crimp slug 76 comprises a shaft 80 and a head 82 and has an longitudinal bore 84 for receiving a threaded stylet 86. The crimp slug 76 and tight-wound conductor 78 are inserted into the bore 74 in the conductive element 72 and an electrical contact between the tight-wound conductor 78 and the conductive element 72 is made by crimps 88. The distal end of the conductive element 72 is encased in a stabilizing shaft 90. The stabilizing shaft 90 comprises an annular hexagonal guide 92 which slides, but does not rotate within the hexagonal chamber 70. Surrounding the distal end of the stabilizing shaft 90 is a conductive cap 94. A bore 96 extends through the conductive cap 94 and the stabilizing shaft 90 into the conductive element 72. A coil 98, on the proximal end of the helix 42, is secured within the bore 96 and makes electrical contact with the conductive element 72.

Those skilled in the art will recognize that the helix can be made non-conducting or that the distal end 16 of the lead 12 near the ring 66 can be made conducting without departing from the spirit of the present invention.

The threaded stylet 86 extends through the length of the lead 12 from a threaded bore 100 in the conductive element 72 to the proximal end of the lead 12, where it emerges from the lead 12 and can be manipulated by a physician during implantation of the lead 12. The stylet 86 can be temporarily screwed into the threaded bore 100 while the lead 12 is being implanted and can be unscrewed and removed from the lead 12 after implantation. With the threaded stylet 86 in place, the tip electrode 22 with its attached helix 42 can be repeatedly extruded from and withdrawn into the silicone sheath 62 at the distal end of the lead 12.

The invention may be embodied in other specific forms without departing from the spirit or essential characteristics thereof. The present embodiment is therefore considered in all aspects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by U.S. Letters Patent is:

1. A lead assembly for implantation in a patient, the assembly comprising:
    an electrode adapted for insertion into a chamber of the patient's heart for electrical stimulation thereof;
    a lead slidably but not rotatably enclosing, at a distal end of the lead, fixation means for securing the electrode to a wall of the heart chamber, said lead also enclosing means for transmitting electrical impulses between a proximal end of the lead and the electrode, the lead having a lumen extending through the lead from the proximal end to the distal end thereof; and
    a removable stylet adapted for insertion in the lumen of the lead for displacing the fixation means along a longitudinal axis of the lead to selectively expose at least part of the fixation means outside the lead or withdraw the fixation means within the lead, said stylet having at a distal end thereof, means for releasably engaging the fixation means at a proximal end thereof and for effecting the exposing and withdrawing of said fixation means, said engaging means comprising a threaded male portion at the distal end of the stylet and the fixation means comprising a threaded bore located near the proximal end of the fixation means.

2. An assembly according to claim 1 wherein the lumen of the lead has a female segment defining a portion of the lumen, said female segment having a polygonal cross-section and wherein the electrode further comprises a polygonal male segment slidably engaging said female polygonal segment.

3. An assembly according to claim 2 wherein the polygonal female segment is a hexagonal female segment and wherein the polygonal male segment is a hexagonal male segment.

4. A lead assembly for implantation in a patient, the assembly comprising:
    an electrode adapted for insertion into a chamber of the patient's heart for electrical stimulation thereof;
    a lead slidably but not rotatably enclosing, at a distal end of the lead, fixation means comprising a sharpened helix, said lead also enclosing means for transmitting electrical impulses between a proximal end of the lead and the electrode, the lead having a lumen extending through the lead from the proximal end to the distal end thereof; and
    a removable stylet adapted for insertion in the lumen of the lead for displacing the fixation means along a longitudinal axis of the lead to selectively expose at least part of the fixation means outside the lead or withdraw the fixation means within the lead, said stylet having at a distal end thereof, means for releasably engaging the fixation means and for effecting the exposing and withdrawing of said fixation means, the lumen of the lead further comprising a female segment defining a portion of the lumen, said female segment having a polygonal cross-section and said electrode further comprising a polygonal male segment slidably engaging said female polygonal segment.

5. An assembly according to claim 4 wherein the polygonal female segment is a hexagonal female segment and wherein the polygonal male segment is a hexagonal male segment.

* * * * *